(12) United States Patent
Vilims (10) Patent No.: US 8,195,307 B2
(45) Date of Patent: Jun. 5, 2012

(54) COMBINATION ELECTRICAL STIMULATING AND INFUSION DEVICE AND METHOD

(76) Inventor: Bradley D. Vilims, Evergreen, CO (US)

(*) Notice: Subject to any disclaimer, the term of this patent is extended or adjusted under 35 U.S.C. 154(b) by 406 days.

(21) Appl. No.: 12/340,092

(22) Filed: Dec. 19, 2008

(65) Prior Publication Data
US 2009/0099613 A1  Apr. 16, 2009

Related U.S. Application Data

(63) Continuation of application No. 11/107,553, filed on Apr. 14, 2005, now abandoned, which is a continuation-in-part of application No. 11/033,591, filed on Jan. 11, 2005, now Pat. No. 7,386,350.

(51) Int. Cl.
*A61N 1/05* (2006.01)
(52) U.S. Cl. ...................................... 607/120
(58) Field of Classification Search .................... 607/50, 607/115–118, 120
See application file for complete search history.

(56) References Cited

U.S. PATENT DOCUMENTS

| | | | |
|---|---|---|---|
| 4,612,934 A | 9/1986 | Borkan | |
| 5,255,691 A | 10/1993 | Otten | |
| 5,342,357 A | 8/1994 | Nardella | |
| 5,397,338 A | 3/1995 | Grey et al. | |
| 5,423,877 A | 6/1995 | Mackey | |
| 5,447,533 A * | 9/1995 | Vachon et al. | 607/120 |
| 5,496,360 A * | 3/1996 | Hoffmann et al. | 607/120 |
| 5,951,546 A | 9/1999 | Lorentzen | |
| 6,002,964 A | 12/1999 | Feler et al. | |
| 6,053,916 A | 4/2000 | Moore | |
| 6,104,957 A | 8/2000 | Alo et al. | |
| 6,136,021 A | 10/2000 | Tockman et al. | |
| 6,141,589 A | 10/2000 | Duhaylongsod | |
| 6,146,380 A | 11/2000 | Racz et al. | |
| 6,148,222 A | 11/2000 | Ramsey | |
| 6,161,047 A | 12/2000 | King et al. | |
| 6,175,769 B1 | 1/2001 | Errico et al. | |
| 6,263,225 B1 | 7/2001 | Howard, III | |
| 6,277,112 B1 | 8/2001 | Underwood et al. | |
| 6,379,349 B1 | 4/2002 | Muller et al. | |

(Continued)

FOREIGN PATENT DOCUMENTS

WO   WO 81/03272   11/1981
(Continued)

OTHER PUBLICATIONS

U.S. Appl. No. 12/033,232, filed Feb. 19, 2008, Vilims.
(Continued)

*Primary Examiner* — Kennedy Schaetzle
*Assistant Examiner* — Erica Lee
(74) *Attorney, Agent, or Firm* — Sheridan Ross, P.C.

(57) ABSTRACT

A combined electrical and chemical stimulation lead is especially adapted for providing treatment to intervertebral discs. The combination lead may be placed proximate to intervertebral disc cellular matrix and nucleus pulposus tissue to promote tissue regeneration and repair, as well as nociceptor and neural tissue modulation. The stimulation lead includes electrodes that may be selectively positioned along various portions of the stimulation lead in order to precisely direct electrical energy to stimulate the target tissue. The lead also includes a central infusion passageway or lumen that communicates with various infusion ports spaced at selected locations along the lead to thereby direct the infusion of nutrients/chemicals to the target tissue. One embodiment utilizes a dissolvable matrix for infusion as opposed to remote delivery through an infusion pump.

11 Claims, 9 Drawing Sheets

U.S. PATENT DOCUMENTS

| | | | |
|---|---|---|---|
| 6,562,033 B2 | 5/2003 | Shah et al. |
| 6,635,054 B2 | 10/2003 | Fjield et al. |
| 6,656,174 B1 | 12/2003 | Hegde et al. |
| 6,662,055 B1 | 12/2003 | Prutchi |
| 6,735,474 B1 | 5/2004 | Loeb et al. |
| 6,827,716 B2 | 12/2004 | Ryan et al. |
| 6,832,115 B2 | 12/2004 | Borkan |
| 6,845,267 B2 | 1/2005 | Harrison |
| 6,847,849 B2 | 1/2005 | Mamo et al. |
| 6,902,547 B2 | 6/2005 | Aves et al. |
| 6,921,403 B2 | 7/2005 | Cragg et al. |
| 6,936,024 B1 | 8/2005 | Houser |
| 7,014,633 B2 | 3/2006 | Cragg |
| 7,065,412 B2 | 6/2006 | Swoyer et al. |
| 7,069,087 B2 | 6/2006 | Sharkey et al. |
| 7,069,094 B2 | 6/2006 | Kubota et al. |
| 7,099,718 B1 | 8/2006 | Thacker et al. |
| 7,169,146 B2 | 1/2007 | Truckai et al. |
| 7,200,446 B2 | 4/2007 | Borkan |
| 7,251,529 B2 | 7/2007 | Greenwood-VanMeerveld |
| 7,276,063 B2 | 10/2007 | Davison et al. |
| 7,309,338 B2 | 12/2007 | Cragg |
| 7,369,894 B2 | 5/2008 | Gerber |
| 7,386,350 B2 | 6/2008 | Vilims |
| 7,422,586 B2 | 9/2008 | Morris et al. |
| 7,449,019 B2 | 11/2008 | Uchida et al. |
| 7,462,178 B2 | 12/2008 | Woloszko et al. |
| 7,771,422 B2 | 8/2010 | Auge et al. |
| 7,819,869 B2 | 10/2010 | Godara et al. |
| 2001/0025175 A1 | 9/2001 | Panescu et al. |
| 2003/0181964 A1 | 9/2003 | Sharkey et al. |
| 2003/0195509 A1 | 10/2003 | Edwards et al. |
| 2003/0195604 A1 | 10/2003 | Ingle et al. |
| 2003/0225331 A1 | 12/2003 | Diederich et al. |
| 2004/0015202 A1 | 1/2004 | Chandler, III et al. |
| 2004/0230273 A1 | 11/2004 | Cates et al. |
| 2004/0236388 A1 | 11/2004 | Gielen et al. |
| 2004/0243206 A1 | 12/2004 | Tadlock |
| 2004/0260277 A1 | 12/2004 | Maguire |
| 2005/0096718 A1 | 5/2005 | Gerber et al. |
| 2005/0177209 A1 | 8/2005 | Leung et al. |
| 2005/0177211 A1 | 8/2005 | Leung et al. |
| 2005/0240238 A1 | 10/2005 | Mamo et al. |
| 2005/0277918 A1 | 12/2005 | Shah et al. |
| 2006/0020297 A1 | 1/2006 | Gerber et al. |
| 2006/0155343 A1 | 7/2006 | Vilims |
| 2006/0217705 A1 | 9/2006 | Godara et al. |
| 2006/0259026 A1 | 11/2006 | Godara et al. |
| 2007/0135881 A1 | 6/2007 | Vilims |
| 2007/0156136 A1 | 7/2007 | Godara et al. |
| 2007/0179536 A1 | 8/2007 | Vilims |
| 2008/0009927 A1 | 1/2008 | Vilims |
| 2008/0172117 A1 | 7/2008 | Skubitz et al. |

FOREIGN PATENT DOCUMENTS

| | | |
|---|---|---|
| WO | WO 94/02077 | 2/1994 |
| WO | WO 95/10320 | 4/1995 |
| WO | WO 98/19613 | 5/1998 |
| WO | WO 99/43263 | 9/1999 |

OTHER PUBLICATIONS

An, et al., "Biological Repair of Intervertebral Disc", SPINE, 2003, vol. 28, No. 15S, pp. S86-S92.

An, et al., "Inrradiscal Administration of Osteogenic Protein-I Increases Intervertebral Disc Height and Proteoglycan Content in the Nucleus Pulposus in Normal Adolescent Rabbits" Spine, vol. 30, No. 1, pp. 25-32.

Ben-Yishay, "News & Highlights—IDET—a new procedure for discogenic back pain", Neuro Spine Website, as early as Sep. 17, 2003, available at http://www.neurospinewi.com/newsletters/IDET. html, printed Dec. 22, 2004, pp. 1-3.

De Mattei, et al., "Effects of Pulsed Electromagnetic Fields on Human Articular Chondrocyte Proliferation", Connective Tissue Research, 2001, vol. 42, No. 4, pp. 269-279.

Ganey, et al., "Disc Chondrocyte Transplantation in a Canine Model: A Treatment for Degenerated or Damaged Intervertebral Disc", SPINE, 2003, vol. 28, No. 23, pp. 2609-2620.

Gruber, et al., "Biologic Strategies for the Therapy of Intervertebral Disc Degeneration", Expert Opinion on Biological Therapy, 2003, vol. 3, No. 8, pp. 1209-1214.

IDET Procedure: IDET (Intradiscal Electrothermal Annuloplasty), thePAINRELIF.com Website, as early as Jul. 13, 2003, available at http://www.thepainrelief.com/idet_idet.shtml, printed on Dec. 22, 2004, pp. 1-2.

"Intradiscal Electrothermal Therapy", emedicine Website, as early as Jun. 14, 2002, available at http://www.emedicine.com/neuro/topic707.htm, printed on Dec. 22, 2004, pp. 1-8.

Matthews, et al., "Treatment of mechanical and chemical lumbar discopathy by dextrose 25%", Journal of Minimally Invasive Spinal Technology, vol. 1, Inaugural 2001, pp. 58-61.

O'Neill et al., "Percutaneous Plasma Decompression Alters Cytokine Expression in Injured Porcine Intervertebral Discs", The Spine Journal, 2004, vol. 4, No. 1, pp. 88-98.

"SpineCath Intradiscal Electrothermal Therapy", SpineUniverse Website, as early as Mar. 29, 2002, available at http://www.spineuniverse.com/displayarticle.php/article217.html, printed Dec. 22, 2004, pp. 1-3.

Walsh, et al., "In Vivo Growth Factor Treatment of Degenerated Intervertebral Discs" Spine, vol. 29, No. 2, pp. 156-163.

Wang, et al., "Up-regulation of Chondrocyte Matrix Genes and Products by Electric Fields", Clinical Orthopaedics and Related Research, Oct. 2004, vol. 427S, pp. S163-S173.

Yoon, et al., "The Effect of Bone Morphogenetic Protein-2 on Rat Intervertebral Disc Cells in Vitro", Spine, vol. 28, No. 16, pp. 1773-1780.

Author Unknown, "Pain Management SInergy™ System"; Baylis Medical Company Inc., 2006, pp. 1-2.

Freeman, et al., "Does intradiscal electrothermal therapy denervate and repair experimentally induced posterolateral annular tears in an animal model?", Spine, Dec. 1, 2003, vol. 28, No. 23, pp. 2602-2608.

International Search Report for International (PCT) Patent Application No. PCT/US06/00312, mailed Jul. 19, 2006.

Written Opinion for International (PCT) Patent Application No. PCT/US06/00312, mailed Jul. 19, 2006.

International Preliminary Report on Patentability for International (PCT) Patent Application No. PCT/US06/00312, issued Jul. 17, 2007.

Supplementary European Search Report for European Patent Application No. 06717501, mailed Mar. 31, 2008.

Partial European Search Report for European Patent Application No. 08101856.6, mailed Jul. 3, 2008.

Partial European Search Report for European Patent Application No. 08151981, mailed Jul. 16, 2008.

Supplementary European Search Report for European Patent Application No. 06717501, mailed Aug. 20, 2008.

Partial European Search Report for European Patent Application No. 08101856.6, mailed Oct. 28, 2008.

Extended European Search Report for European Patent Application No. 08151981.1, dated Dec. 9, 2008.

Ahadian, "Pulsed radiofrequency neurotomy: advances in pain medicine," Current Pain and Headache Reports, 2004, vol. 8, pp. 34-40.

Akatov et al., "Percutaneous radiofrequency destruction of the obturator nerve for treatment of pain caused by coxarthrosis," Stereotact Funct Neurosurg, 1997, vol. 69(1-4 Pt 2), pp. 278-280 (Abstract only).

Anis et al., "Use of radio-frequency ablation for the palliative treatment of sacral chordoma," Am. J. Neuronadiol, 2004, vol. 25, pp. 1589-1591.

Atlihan et al., "Anatomy of the Anterior Sacroiliac Joint With Reference to Lumbosacral Nerves," Clinical Orthopaedics and Related Research, 2000, No. 376, pp. 236-241.

Buijs et al., "Radiofrequency treatment of sacroiliac joint-related pain aimed at the first three sacral dorsal rami: a minimal approach," The Pain Clinic, 2004, vol. 16(2), pp. 139-146.

Calvillo et al., "Anatomy and Pathophysiology of the Sacroiliac Joint," Current Review of Pain, 2000, vol. 4, pp. 356-361.

Cohen et al., "Lateral Branch Blocks as a Treatment for Sacroiliac Joint Pain: a Pilot Study," Regional Anesthesia and Pain Medicine, 2003, vol. 28(2), pp. 113-119.

Cohen et al., "Pulsed radiofrequency as a treatment for groin pain and orchialgia," Urology, 2003, vol. 61(3), pp. 645xxi-xxiii.

Cohen, "Sacroiliac Joint Pain: A Comprehensive Review of Anatomy, Diagnosis, and Treatment," Anesthesia & Analgesia, 2005, vol. 101(5), pp. 1440-1453.

Cole et al., "The Sacroiliac Joint: A Functional Approach," Critical Reviews in Physical and Rehabilitation Medicine, 1996, vol. 8(1&2), pp. 125-152.

Conaghan et al., "Sacral nerve stimulation can be successful in patients with ultrasound evidence of external anal sphincter disruption," Diseases of the Colon and Rectum, 2005, vol. 48(8), pp. 1610-1614.

Davis et al., "Radiofrequency Treatment in the United States," Pain Practice, 2002, vol. 2(3), pp. 192-194.

Deer, "Chapter 6: Injections for the Diagnosis and Treatment of Spinal Pain," American Society of Anesthesiologists, Inc., 2004, vol. 32, pp. 53-69.

Dreyfuss et al., "Chapter 32: Radiofrequency Neurotomy of the Zygapophyseal and Sacroiliac Joints," Pain Procedures, 2000, pp. 395-420.

Ebraheim et al., "Anatomic Considerations for Posterior Approach to the Sacroiliac Joint," Spine, 1996, vol. 21(23), pp. 2709-2712.

Ferrante et al., "Radiofrequency sacroiliac joint denervation for sacroiliac syndrome," Regional Anesthesia and Pain Medicine, 2001, vol. 26(2), pp. 137-142.

Fortin et al., "Three Pathways between the Sacroiliac Joint and Neural Structures," Am. J. Neruoradiol., 1999, vol. 20, pp. 1429-1434.

Fortin et al., "Sacroiliac Joint Innervation and Pain," The American Journal of Orthopedics, 1999, pp. 687-690.

Fukui et al., "Successful relief of hip joint pain by percutaneous radiofrequency nerve thermocoagulation in a patient with contraindications for hip arthroplasty," Journal of Anesthesia, 2001, vol. 15, pp. 173-175.

Gevargez et al., "CT-guided percutaneous radiofrequency denervation of the sacroiliac joint," Eur Radiol., 2002, vol. 12, pp. 1360-1365.

Gopalani et al., "A novel technique for treating nonsurgical hip pain with radiofrequency lesioning of the sensory branches of the obturator and femoral nerves: a case report," Archives of Physical Medicine and Rehabilitation, Poster 102, 2003, vol. 84, A23.

Jiang et al., "Comparison between radiofrequency coagulation plus small needle knife and single method in treatment of sacrolumbar pain," Chinese Journal of Clinical Rehabilitation, 2003, vol. 7(20), pp. 2844-2845 (Abstract only).

Kawaguchi et al., "Percutaneous radiofrequency lesioning of sensory branches of the obturator and femoral nerves for the treatment of hip joint pain," Regional Anesthesia and Pain Medicine, 2001, vol. 26(6), pp. 576-581.

Kirkham et al., "Neuromodulation through sacral nerve roots 2 to 4 with a Finetech-Brindley sacral posterior and anterior root stimulator," Spinal Cord, 2002, vol. 40(6), pp. 272-281.

Kirsch et al., "Proton radiotherapy for Hodgkin's disease in the sacrum," Lancet Oncology, 2005, vol. 6, pp. 532-533.

Kline et al., "Chapter 19: Radiofrequency techniques in clinical practice," Interventional Pain Management, 2001, pp. 243-290 (2001).

Leng et al., "How sacral nerve stimulation neuromodulation works," Urol. Clin. North. Am., 2005, vol. 32(1), pp. 11-18 (Abstract only).

Liguoro et al., "The Posterior Sacral Foramina: An Anatomical Study," 1999, J. Anat., vol. 195, pp. 301-304.

Murata et al., "Origin and pathway of sensory nerve fibers to the ventral and dorsal sides of the sacroiliac joint in rats," Journal of Orthopaedic Research, 2001, vol. 19, pp. 379-383.

Plancarte et al., "Radiofrequency Procedures for Sacral and Pelvic Region Pain," Pain Practice, 2002, vol. 2(3), pp. 248-249.

Pino et al., "Morphologic analysis of bipolar radiofrequency lesions: implications for treatment of the sacroiliac joint," Regional Anesthesia and Pain Medicine, 2005, vol. 30(4), pp. 335-338.

Raj et al., "Executive Summary: The Current Status of the Practice of Radiofrequency in the World," Pain Practice, 2002, vol. 2(3), pp. 176-179.

Simon, "Chapter 50: Sacroiliac joint injection and low back pain," Interventional Pain Management, 2001, pp. 535-539.

Slipman et al., "Sacroiliac Joint Syndrome," Pain Physician, 2001, vol. 4(2), pp. 143-152.

Valleylab-RF Pain Management System, Sep. 16, 2004, available at internet archives, http://www.valleylab.com/static/pain/products-generator.html, 2 pages.

Van Zundert et al. "Application of Radiofrequency Treatment in Practical Pain Management: State of the art," Pain Practice, 2002, vol. 2(3), pp. 269-278.

Yin et al., "Sensory stimulation-guided sacroiliac joint radiofrequency neurotomy: technique based on neuroanatomy of the dorsal sacral plexus," Spine, 2003, vol. 28(20), pp. 2419-2425.

U.S. Appl. No. 13/088,558, filed Apr. 18, 2011, Vilims.

U.S. Appl. No. 13/271,312, filed Oct. 12, 2011.

* cited by examiner

COMBINATION ELECTRICAL STIMULATING AND INFUSION DEVICE AND METHOD

CROSS REFERENCE TO RELATED APPLICATION

This application is a continuation of CIP application Ser. No. 11/107,553, filed on Apr. 14, 2005, which is a continuation-in-part of U.S. Pat. No. 7,386,350, issued on Jun. 10, 2008, entitled "Combination Electrical Stimulating and Infusion Medical Device", the disclosure of which is hereby incorporated by reference herein.

TECHNICAL FIELD OF THE INVENTION

The present invention relates generally to electrical stimulation leads and chemical infusion catheters for treatment of medical conditions, and more particularly, to a system, method and device for providing combined electrical stimulation and chemical/drug infusion for treatment of intervertebral disc ailments.

BACKGROUND OF THE INVENTION

It is known that immersing certain cell types within an electrical field will cause these cells to proliferate thus facilitating tissue repair. One known use of an electrical field for such repair is "in bone" stimulators that are implanted in fractures and/or spinal fusions. Another type of treatment has recently been developed for spinal conditions wherein target tissue is stimulated by an electrical lead using radio-frequency energy to induce a thermal lesion in the target tissue. In this type of procedure, the therapeutic benefit is intended to derive from heating the target tissue and not from immersing the tissue in an electric field. Thus, the electrical lead in this treatment is strictly for use in heating the tissue, and there is no therapeutic electrical field generated. Chemical treatment of target tissues has also been developed by use of various types of infusion catheters.

For both electrical and thermal stimulation, an electrical current generator, commonly referred to as a pulse generator, may be used to transmit a pulse of electrical current to an implanted stimulation lead that has been precisely placed to transmit the electrical or thermal energy from the electrodes to the target tissue in order to treat the particular condition. For chemical stimulation, one or more drugs or nutrients are delivered by a pump that transfers a desired quantity and frequency of the drug/nutrient through an infusion port of the catheter to the target tissue. For chemical stimulation as well as electrical/thermal stimulation, implanted pumps and generators can be used to deliver the electrical and chemical stimulation as opposed to transdermal delivery devices. More particularly, implanted pulse generators (IPG) as well as implanted drug dispensers (IDP) are commonly used so that patients do not have to return to a medical facility each time treatment is to be conducted.

The intervertebral disc (IVD) provides separation, shock absorption, and controlled motion between vertebral bodies. The disc is comprised of a central nucleus of a semi-fluid mass of mucoid material, (nucleus pulposus), an outer more dense collagen ring (annulus fibrosis), and a thin, metabolically active cellular layer separating the nucleus and the outer collagen ring, referred to as the annular nuclear interface/transitional zone. Disc nutrition is tenuous at best and is provided by diffusion through the vertebral end plate in contact with the outer surface of the disc. As a result, a disc has limited ability to heal or regenerate. Due to age, injury or other conditions, cracks or fissures may develop in the wall of invertebral discs causing a chronic source of pain in many patients. Additionally, the inner disc tissue (nucleus) will frequently cause the disc to bulge or herniate into the fissures in the outer region of the disc, thus causing nerve tissue therein to generate pain signals.

Current treatment for such disc disorders include analgesics, physical therapy and epidural steroid injections. Success with these treatments is frequently disappointing and the patient will all too often have to undergo spinal fusion. Spinal fusion is a very invasive, bio-mechanically altering, and marginally effective treatment.

One relatively new procedure has been developed to treat such disc ailments and general discogenic back pain. As an alternative to other surgical procedures for patients who suffer from back pain caused by certain types of disc disorders, this new procedure is made possible by use of thermal stimulation leads that provide precise temperature control in the delivery of thermal energy to target tissue. This procedure, commonly referred to as intradiscal electrothermal annuloplasty (IDET) was initially believed to function by cauterizing nerve endings within the disc wall to assist in reduction of pain, and the heat produced by the stimulation leads would also thicken the collagen of the disc wall thereby promoting healing of the damaged disc. IDET has proven in some cases to be a minimally invasive procedure to treat these types of disc ailments. However, recent research, and clinical experience has cast doubt as to the exact method of action. More specifically, for percutaneous treatments like IDET, the general operating premise in these procedures, is to heat, either through conduction or induction, causing collagen restructuring and nociceptor coagulation within the disc that would stabilize the structure, and dennervate the painful discs while retaining the motion segment and thus reduce the need for fusion. While these procedures have proven more effective than placebo, the results are far from acceptable. Research has demonstrated that collagen modulation and nociceptor coagulation is unlikely to be the mechanism of action, and that these devices may simply create injury patterns, that in a small subset of patients, stimulates a regenerative response, thereby accounting for the better than placebo results.

Combination electrical stimulators and chemical infusion catheters are known for purposes of treating various spine and brain ailments. One reference that discloses such a combination device is the invention in U.S. Publication No. US2004/0243206. This reference specifically discloses a combination electrical and stimulation lead for stimulation of a person's nerve tissue in the brain. One or more electrodes are located along the lead body and are adapted to be positioned proximate the target nerve tissue and to deliver electrical stimulation pulses transmitted through the lead to the target nerve tissue. One or more infusion ports located along the lead body are adapted for placement proximate the target nerve tissue and to deliver chemical stimulation pulses transmitted through the lead to the target nerve tissue.

While combination electrical and stimulation leads may be known, special considerations must be made for use of such devices for intervertebral disc treatment.

Placement of a stimulation lead within a disc can be quite difficult. Because a disc does not have a uniform density, known stimulation leads can be quite difficult to place and may require the attending physician to make multiple attempts for proper placement or abandon the procedure. Of course, multiple placement attempts greatly increase the invasive nature of the procedure and therefore create unnecessary tissue damage and increased risk. Inability to perform the procedure denies the patient a therapeutic option. Improper placement of the stimulation lead can also result in the undesirable damage of nerve tissue that is not contributing to the chronic pain or other ailments. Because of the overall metabolically inactive nature of the disc, it is also important that chemical infusion be precisely targeted to contact the damaged area of the disc with the delivered chemicals/nutrients, otherwise inaccurate delivery to non-damaged portions of the disc can reduce the effectiveness of the procedure. Thus, there is a need for a combination electrical and chemical stimulation lead that can be precisely placed with a high rate of success on a first attempt.

The IVD is also a motion segment of the body that is subjected to many flexion/extension/rotation cycles every day. In some procedures, it may be necessary to keep the stimulation lead emplaced for long periods of time, such as weeks or perhaps months. Thus, it is desirable to have a stimulation lead that maintains a small profile, yet is resilient enough to withstand the risk of permanent deformation or shearing during treatment and removal of the stimulation lead after treatment.

SUMMARY OF THE INVENTION

In accordance with the present invention, a combined electrical and chemical stimulation device is provided that is especially adapted for treatment of intervertebral disc ailments. The stimulation device is in the form of a stimulation lead designed to be placed in the disc percutaneously through an introducer needle using an extra-pedicular approach; however, micro-surgical or open-surgical techniques may also be utilized. More specifically, the device of the present invention is specifically designed to facilitate placement proximate to the metabolically active cellular, nuclear, annular interface layer by use of one or more selected embodiments including a straight, curved or bent tip, as well as a variable stiffness tip. Selection of one of these embodiments allows the physician to precisely navigate the lead through the nucleus of the disc. In yet another embodiment of the present invention, the stimulation lead may be placed directly into the nuclear annular interface by use of a introducer needle having a bent tip, and use of a stimulation lead having a straight tip that can take a substantially linear path to reach the target tissue.

The structure of the stimulation lead of the present invention is characterized by an elongate and tubular shaped body including one or more electrodes located along selected portions of the lead body and adapted for positioning proximate the target tissue to deliver electrical stimulation pulses transmitted through the lead. Preferably, the electrodes extend circumferentially around a selected length or portion of the lead since it is difficult to orient a specific lateral side of the lead against target tissue. One or more infusion ports are also located along the lead body and are adapted to be positioned proximate the target tissue to deliver selected chemicals/nutrients.

Once the stimulation lead is correctly positioned, the lead is then connected to a pulse generator for delivery of electrical energy to the electrodes located on the distal portion of the stimulation lead, and is connected to an infusion pump that provides a controlled delivery of chemicals/nutrients through the lead to the target tissue. Preferably, the electrical pulse generator and infusion pump are implanted medical devices. These devices are also preferably refillable and rechargeable. Another generally desirable characteristic of pulse generators includes those having a capability to produce either constant or variable current. It is also desirable to provide electrical contacts/electrodes that are linked in series, parallel, or combinations thereof which allow selective activation of all or a selected group of the electrodes. Other desirable general characteristics for an infusion pump are those pumps which (i) control infusion material at either a constant or variable rate, and at a constant or variable pressure, (ii) provide automatic compensation for varying infusion pressures, and (iii) have anti-back flow capability to prevent backflow of infusion material through the stimulation lead, as well as pressure safety valves to compensate for overpressure situations. Furthermore, the pump, pulse generator and stimulation lead may be coated with an antibacterial coating to decrease the risk of infection. The pulse generator and pump may also incorporate appropriate alarms to notify of infusion and stimulation failure/abnormality.

Particular embodiments of the present invention provide one or more advantages in terms of navigation of the stimulation lead, as well as placement of the infusion ports and electrodes for effectively delivering electrical and chemical treatment. More specifically, the particular shape of the stimulation lead, as well as the particular placement of the electrodes and infusion ports are especially adapted for delivering the electrical stimulation and chemical infusion to target tissue within a disc. A stiffening or support element may be incorporated in the wall of the stimulation lead to ensure the lead does not prematurely shear or otherwise structurally fail during use and removal. The stiffening element is preferably in the form of an elongate support that extends longitudinally within the wall of the stimulation lead and terminating near the distal tip of the lead.

Further advantages and features of the present invention will become apparent from a review of the following detailed description, taken in conjunction with the drawings.

BRIEF DESCRIPTION OF THE DRAWINGS

Reference is now made to the following detailed description taken in conjunction with the accompanying drawings in order for a more thorough understanding of the present invention.

DETAILED DESCRIPTION

Figure 1:
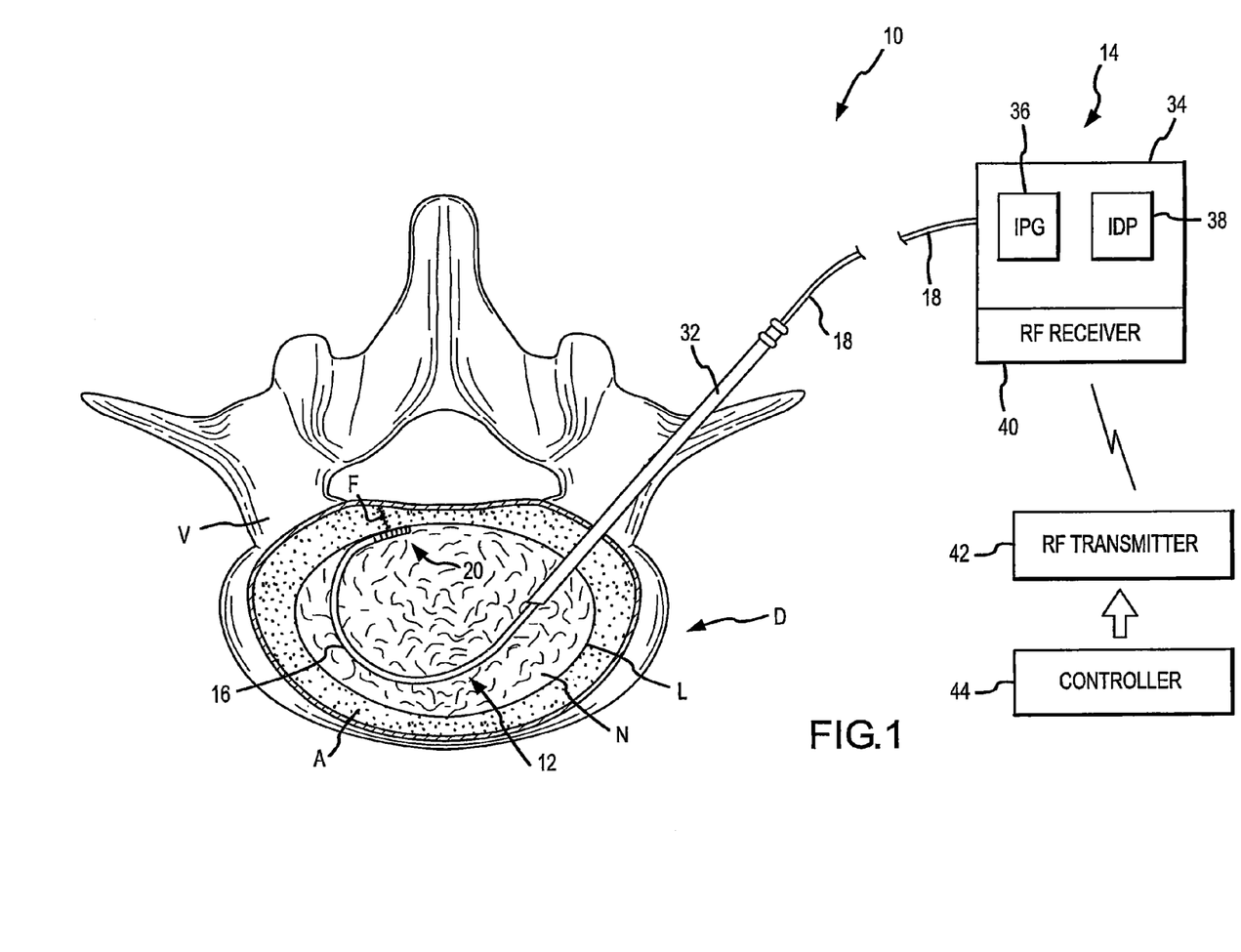
FIG. 1 illustrates the system of the present invention including a stimulation lead inserted in an intervertebral disc, and a stimulation source that provides a controlled delivery of electrical field energy and chemicals/nutrients through the stimulation lead.
Figure 2:
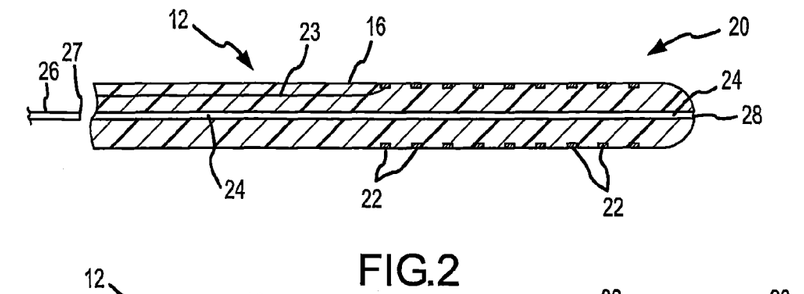
FIG. 2 is a greatly enlarged cross-section of the working distal portion of one preferred embodiment of the stimulation lead of the present invention.

Referring to FIGS. 1 and 2, the system 10 of the present invention is shown that includes a combination electrical and chemical stimulation device 12, a stimulation source 14 that communicates with the stimulation device 12 for delivering electrical energy and chemicals to the stimulation device, and an interventional device such as an introducer needle 32 that allows introduction of the stimulation lead into the disc. The stimulation device 12 is shown as inserted within an intervertebral disc D. The combination device 12 more particularly includes a percutaneous electrical and chemical stimulation lead 16 in the form of an elongate tubular member having a desired length and diameter allowing the lead 16 to be placed within the intervertebral disc of the patient to be treated. The working distal portion 20 of the stimulation lead 16 provides the desired stimulation through a plurality of electrodes 22 which are selectively positioned on the distal portion 20, along with a plurality of infusion ports 30 which allow delivery of chemicals/nutrients to target tissue. The proximal portion of the stimulation device 12 can be referred to as a lead extension 18 that connects to the stimulation source 14. The lead extension 18 can be made of the same type and diameter material as the stimulation lead 16, or may be made of a different type of material and diameter.

Referring specifically to FIG. 2, in a first embodiment of the stimulation lead, a plurality of circumferentially extending electrodes 22 are positioned at the distal portion 20. The electrodes 22 are also spaced longitudinally along the distal portion 20. The electrodes produce an array of electrical field energy, and the target tissue is immersed in the electrical field. One or more electrical conductors 23 extend through the interior of the stimulation lead 16 in order to transmit the electrical impulses to the electrodes 22. It is preferable to utilize a single conductor 23 along the major length of the lead, and then provide branch conductors (not shown) at the distal portion 20 that then extend to contact the various electrodes. The branch conductors could be a linearly arranged set of wire extensions extending between each electrode, or any other advantageous combination of wire conductors to interconnect the electrodes. Use of a single conductor is a more robust design as opposed to multiple smaller conductors that are more prone to breakage as a result of the motion cycles of the ISD. It is also contemplated that the electrode could be a single electrode wound in a helical pattern about the distal portion 20. Thus in this helical pattern, only one conductor 23 would be required with no additional branch conductors. In order to generate the desired intensity and size electrical field, the electrodes 22 can be disposed on the distal portion in a pattern or arrangement that best suits the electrical field to be generated. For example, in the helical pattern, the electrode could be wound with a tighter pattern to generate a more intense field, while a looser more spaced pattern would generate a less intense field. Of course, the particular signal or impulse current provided to the electrodes also determines the intensity of the field generated.

In order to provide chemical infusion, a central lumen or passageway 24 is formed through the stimulation lead. The central lumen 24 may extend completely through the lead thereby forming a distal opening 28 in the stimulation lead and providing one infusion port that is directed distally of the stimulation lead.

The stimulation lead 16 may be made of a homogeneous material, or may be made of differing materials that cause the stimulation lead to have either a more progressively stiff or more progressively flexible characteristic as the lead extends in the distal direction. Depending upon the manner in which the stimulation lead is to be emplaced, it may be desirable to use either the more progressively stiff or more progressively flexible arrangement.

In accordance with the method of the present invention, a stylet (not shown) is first inserted through the introducer needle 32. The introducer needle 32 is emplaced by penetrating the skin and muscle tissue, and ultimately into the disc D. When the introducer needle has penetrated the disc, the stylet is removed and the stimulation lead 16 is then inserted through the lumen of the introducer needle.

Referring again to FIG. 1, the stimulation lead 16 is illustrated as being emplaced within the disc D. This disc D is shown in cross section along with an adjacent vertebra V. The stimulation lead 16 is shown as taking an arcuate or curved path through the disc nucleus N in order to be precisely positioned at the area of the disc to be treated, illustrated as a fissure F which has developed adjacent the spinal fluid sac (not shown). The other primary features of the disk D are also illustrated including the annulus fibrosis A and the thin layer L defining the annular nuclear interface/transitional zone.

The stimulation source 14 is preferably an implantable medical device 34 including both an IPG (implantable pulse generator) 36 and an IDP (implantable drug dispenser) 38. The implantable device 34 could be contained within a single structural housing, or two separate housings, one for the IPG 36, and one for the IDP 38. The IPG and IDP can both be self-contained devices with internal control for preset delivery of electrical and chemical pulses. Alternatively, an external controller 44 could be used to modify the desired treatment protocol by use of RF transmission wherein an implantable RF receiver 40 is integrated with the IPG 36 and IDP 38. The RF receiver 40 could also be housed within the same implantable medical device 34, or could be a separate implanted device. An external RF transmitter 42 transmits RF signals to control the delivery of electrical stimulation and chemicals to the stimulation lead 16. A controller 44 provides the specific instruction set for transmission by the RF transmitter 42.

In accordance with the apparatus and method of the present invention, there are a number of nutrients and medications that can be delivered by the stimulation lead. For nutrients, this list includes, but is not limited to, glucose, glucosamine, chondroitin, oxygen and oxygenating agents, anti-oxidants, anti-glycosylating agents, and pH buffers. For medications, these may include, without limitation, anti-inflammatory agents and growth factors, such as growth and differentiating factor-5 (GDF-5), transforming growth factor-beta (TGF-β), insulin-like growth factor-1 (IGF-1), and basic fibroblasts growth factor (bFGF). In terms of the types of electrical impulses provided to the electrodes 22, these electrical impulses may be continuous or variable over time, and may vary based upon voltage, amperage, and alternate current frequency.

Figure 3:
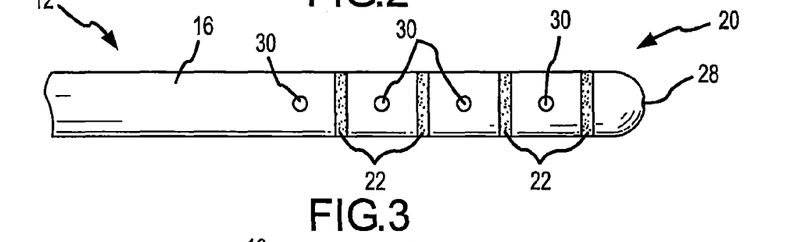
FIGS. 3-7 are greatly enlarged side or elevation views illustrating other preferred embodiments of the stimulation lead.

Referring to FIG. 3, a different arrangement is illustrated with respect to the location of the electrodes 22, and the single infusion port at distal opening 28 is supplemented with a plurality of additional infusion ports 30. In this embodiment, fewer electrodes are incorporated, yet additional infusion ports 30 are provided that are spaced longitudinally along the length of the lead 16 and placed between the electrodes 22.

Figure 4:
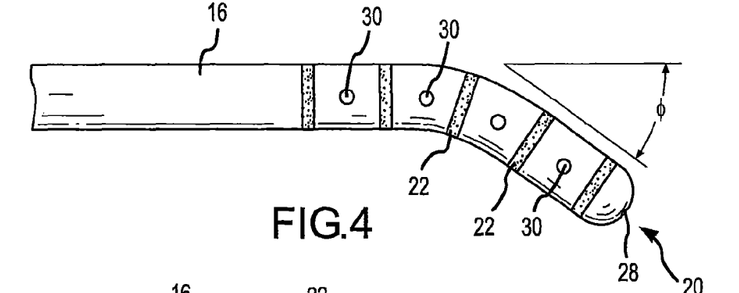

FIG. 4 shows another embodiment with a different arrangement of electrodes 22 and infusion ports 30 as well as a modification of the stimulation lead shape to include a bent distal tip having a chosen bend angle Ø. The bend angle Ø helps define the path of travel of the lead within the disc nucleus during emplacement. In other words, imparting a particular bend angle on the distal tip of the stimulation lead causes the stimulation lead to travel in an arcuate path such as shown in FIG. 1. Imparting a greater bend angle on the lead results in the stimulation lead traveling in a tighter arcuate path, while imparting a lesser bend angle generally results in the stimulation lead traveling in a broader arc or arcuate path.

Figure 5:
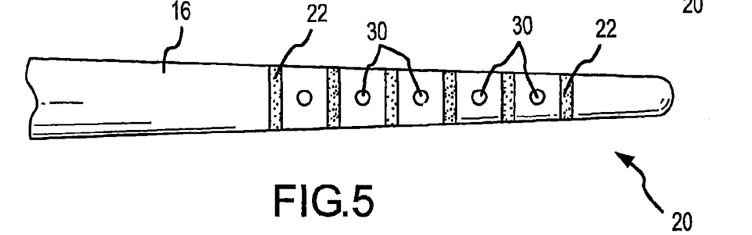

Referring to FIG. 5, another embodiment of the stimulation lead is illustrated wherein the lead has a progressively narrowing diameter towards the distal end thereof. With this type of stimulation lead, travel of the lead through the more dense annulus tissue is facilitated because the distal tip has a smaller frontal profile and is more easily controlled.

Figure 6:
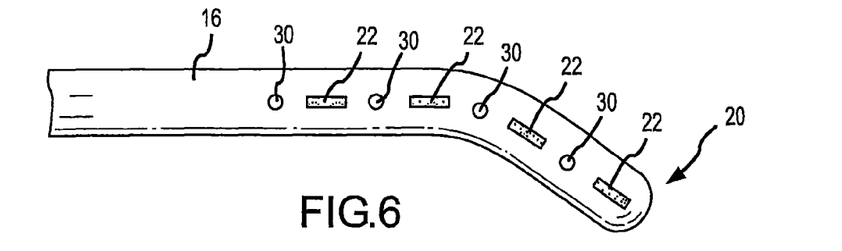

Referring to FIG. 6, yet another embodiment of the stimulation lead is illustrated wherein the electrodes 22 are not formed circumferentially around the distal portion 20, but are formed more linearly along one side of the stimulation lead. Additionally, the infusion ports 30 may have more of an oval shape and be larger in size which facilitates greater volumetric infusion. This embodiment may be preferred when it is desired to more precisely direct the array of electrical energy to the target tissue. The electrical energy array that is created by circumferentially arranged electrodes result in transmission patterns having a radial or circular pattern extending away from the stimulation lead. Thus, a plurality of circumferentially arranged electrodes transmit energy in all directions to tissue that surrounds the stimulation lead. On the contrary, locating the electrodes only along one side or edge of the stimulation lead results in transmission of energy in a more linear and less radial pattern, and directed primarily orthogonal or perpendicular to the axis of the stimulation lead. The embodiment of FIG. 6 also illustrates the distal end as being bent at a desired angle.

Figure 7:
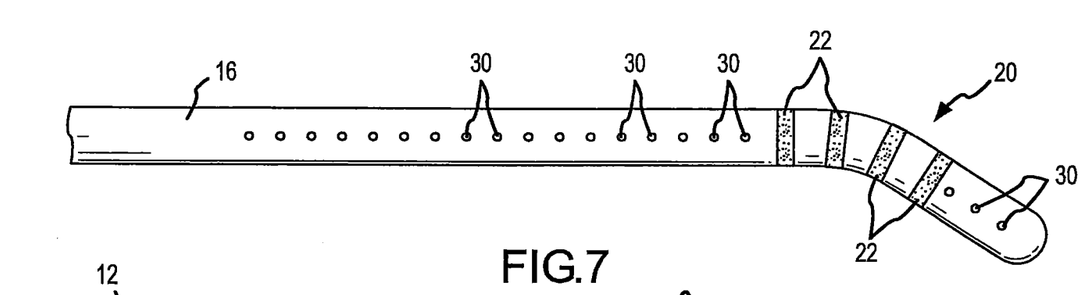

FIG. 7 illustrates yet another embodiment of the stimulation lead wherein the electrodes 22 are concentrated at a particular location, and the infusion ports 30 are spaced in a pattern extending a greater longitudinal length of the lead. A stimulation lead in this particular arrangement may be particularly suitable for repair of a fissure located at a very defined position within the disc, yet if the disc shows great overall degeneration, it is preferable to provide nutrients to a greater length of the annulus whereby the infusion ports 30 can distribute nutrients to a greater length of the annulus.

Figures 8, 9:
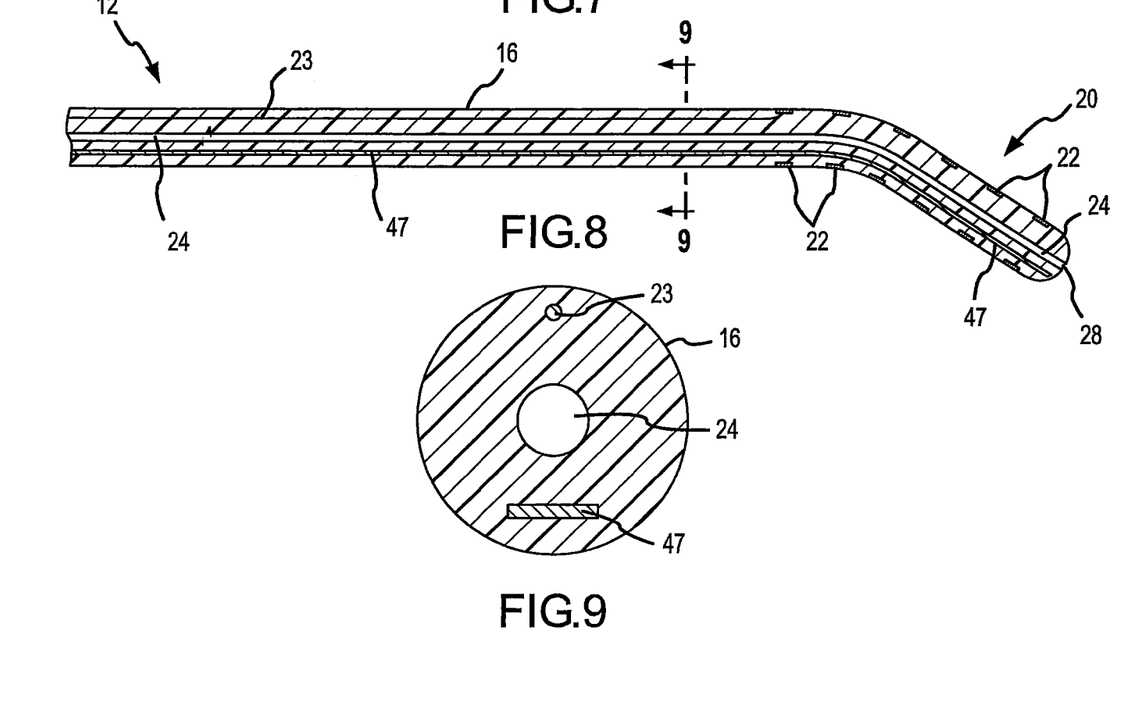
FIG. 8 is a greatly enlarged cross-section of the working distal portion of another preferred embodiment that incorporates a stiffening element.
FIG. 9 is a section taken along line 9-9 of FIG. 8.

FIG. 8 illustrates yet another preferred embodiment of the present invention wherein a stiffening or strengthening member 47 is incorporated within the structural wall of the stimulation lead to provide increased strength to the lead without enlarging the frontal profile of the lead. As shown, the stiffening member 47 is an elongate member that extends longitudinally through the wall of the lead and terminates near the distal end thereof. The stiffening member is malleable to a degree that allows the lead to maintain some desired flexibility during emplacement, but increases the overall shear and torsional strength of the lead to prevent premature failure after emplacement or during removal. The member 47 could be made of a selected metal or thermoplastic approved for medical use.

Figure 10:
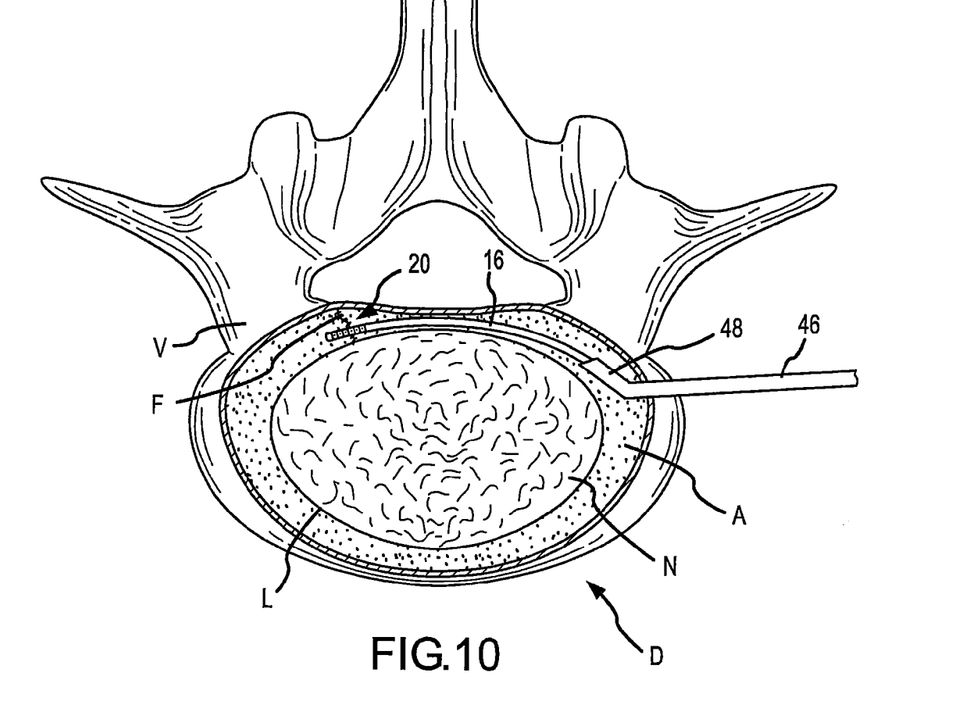
FIG. 10 illustrates another preferred embodiment of the present invention in the form of an introducer needle having a bent distal end for placement of the stimulation lead directly into the nuclear annular interface.

Referring to FIG. 10, yet another embodiment of the invention is shown wherein an introducer needle 46 is not placed within the disc nucleus, but rather is placed only into the disc annulus, and then the stimulation lead 16 extends through the disc annulus to the target tissue, also shown as a fissure F. In this embodiment, it is preferable that the stimulation lead 16 exits the introducer needle through a bent distal portion 48 so that the lead travels in a more parallel fashion within the annulus and along a more linear path to the target tissue. Accordingly, a stimulation lead having a straight tip like shown in FIGS. 2, 3 and 5, would be more suitable according to this embodiment. In the event the distal opening 28 of the lead 16 is of a size which could allow nuclear tissue to clog or block the distal opening 28, a guide wire 26 (see FIG. 12) may be inserted through the lumen 24 of the lead 16, and the distal tip 27 of the guide wire could be placed flush with the distal opening 28 in order to prevent clogging of the distal opening 28, as well as to provide additional rigidity for placement of the stimulation lead 16. If the guide wire 26 is used, then the guide wire 26 is removed prior to connecting the stimulation lead 16 to an IDP and/or IPG. Also, the central lumen may terminate before passing through the distal tip of the lead. Thus, all of the infusion ports 30 would be arranged on the lead to direct chemicals/nutrients in a perpendicular direction away from the axis of the lead.

Figure 11:
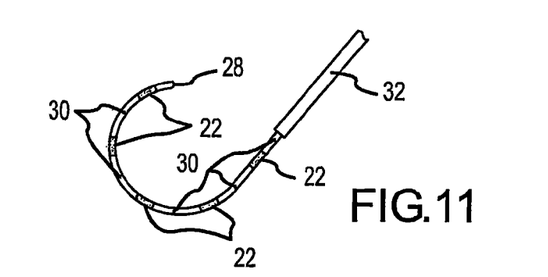
FIGS. 11-13 illustrate further embodiments of the present invention wherein the electrodes and infusion ports are dispersed substantially along the entire length of the stimulation lead.
Figure 12:
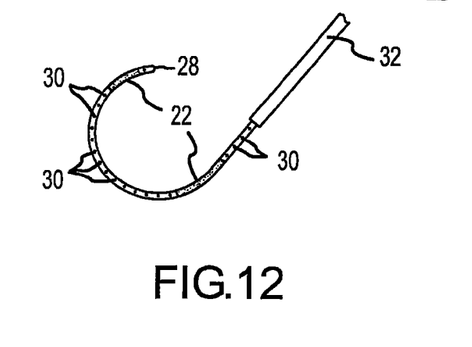
Figure 13:
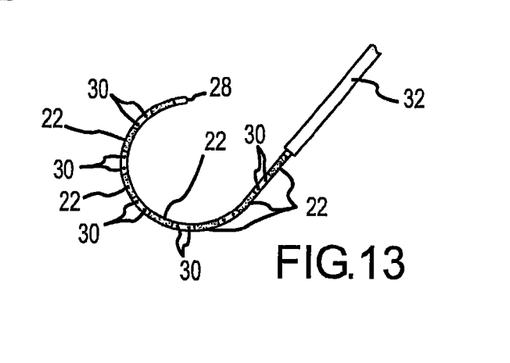

FIGS. 11-13 illustrate yet further embodiments of the present invention wherein the electrodes 22 and infusion ports 30 are dispersed along substantially the entire length of the stimulation lead. In many cases, the disc to be treated has undergone such great degeneration that the entire disc is in need of treatment, as opposed to a more minor degenerative condition such as a single localized fissure. In such cases, it is advantageous to provide both electrical and chemical stimulation to as much of the disc as possible. The embodiments at FIGS. 11-13 show various combinations of the electrodes 22 and ports 30 that provide greater dispersion of the electrical and chemical stimulation. Specifically, the electrodes are larger and are spread out along a greater length of the lead. The infusion ports are also spread out along a greater length of the lead.

Figure 14:
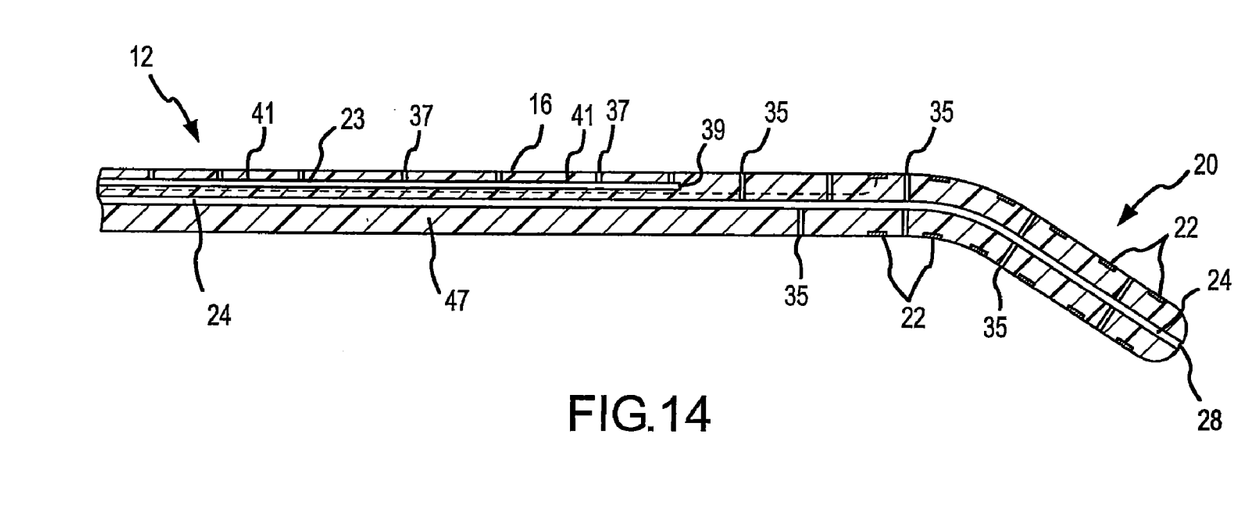
FIG. 14 illustrates a cross section of a further embodiment of the present invention wherein a dual lumen is provided enabling greater selective control of infusion through designated portions of the stimulation lead.

FIG. 14 illustrates yet another embodiment of the invention wherein a second lumen 41 is incorporated within the stimulation lead to provide greater infusion selectivity. More specifically, FIG. 14 shows that the second lumen 41 terminates at end 39 which is intermediate between the distal tip of the stimulation lead and the proximal end thereof. This lumen 41 communicates with the set of infusion ports 37 which are spaced from the end 39 of the lumen 41 towards the proximal end of the lead. The first or central lumen 24 then communicates with the infusion ports 35 that are located distally of the end 39 of the second lumen 41.

During treatment, it may be desirable to administer nutrients and/or medications to different parts of the disc being treated. Furthermore, it may be desirable to provide the nutrients/medications to these different locations within the disc at differing flow rates and at differing times and frequencies. With the provision of a dual set of lumens, a physician has the ability to selectively control infusion to two distinct areas within the disc, and can vary the treatment protocol between the two areas of the disc by selecting the particular dosing, frequency, and makeup of the infusion material to the distinct locations within the disc. This selective treatment capability may be advantageous where, for example, the distal end of the stimulation lead may be placed near the interface/transitional zone, and the tissue extending therealong together with the annulus fibrosis may have particular needs in terms of the required type of nutrients and/or medication, while the tissue within the nucleus may have slightly different needs. Thus, the embodiment at FIG. 14 provides the treating physician with additional options in providing effective treatment.

The particular sizes of the lumens, as well as the sizes and spacing of the openings 35 and 37 may be configured for optimal delivery of various types of infusion material. For example, assuming that the desired nutrient/medication to be delivered to the distal end of the stimulation lead was fairly viscous, it may be advantageous to provide the lumen 24 with a larger cross-sectional size, as well as to provide the infusion openings 35 of an increased size to accommodate the higher viscosity. As a further example, if the lumen 41 was to deliver a less viscous nutrient/medication, then the lumen 41 would preferably have a smaller cross-sectional area, and the openings 37 would preferably be smaller than the openings 35. Thus, one convenient way in which to control infusion is to advantageously arrange the particular size, number, and spacing of the infusion openings as well as the size of the lumens which deliver the infusion material through the openings.

It is further contemplated within the present invention to also provide non-uniform lumens, as well as infusion openings that vary in size within the same supplying lumen. As discussed above, the IDP 38 may be programmed for preset delivery of chemical "pulses". The IDP 38 is typically programmed to be in an "on" or "off" state to generate delivery of a set amount of fluid over a specific period of time. However, once the infusion material is released from the IDP, the IDP itself does not have control over the way in which the infusion material is dispersed through the stimulation lead. Assuming that a lumen of a stimulation lead has a uniform diameter with infusion openings also being of a uniform diameter, then the infusion ports located at the more proximal end of the device will most likely deliver a greater amount of material to the disc as opposed to the infusion ports located at the distal end of the device because there will be an inherent loss in the amount of fluid delivered downstream based on frictional losses within the lumen and the upstream openings communicating with the lumen. Therefore, in order to ensure equal distribution of infused material, it may be desirable to provide a lumen having a diameter that progressively enlarges as it extends towards the distal end of the device. Alternatively or in combination with the progressively changing lumen size, it may be desirable to provide infusion ports toward the proximal end of the device that are slightly smaller than the infusion ports located towards the distal end of the device to further help compensate for any frictional line losses.

Figure 15:
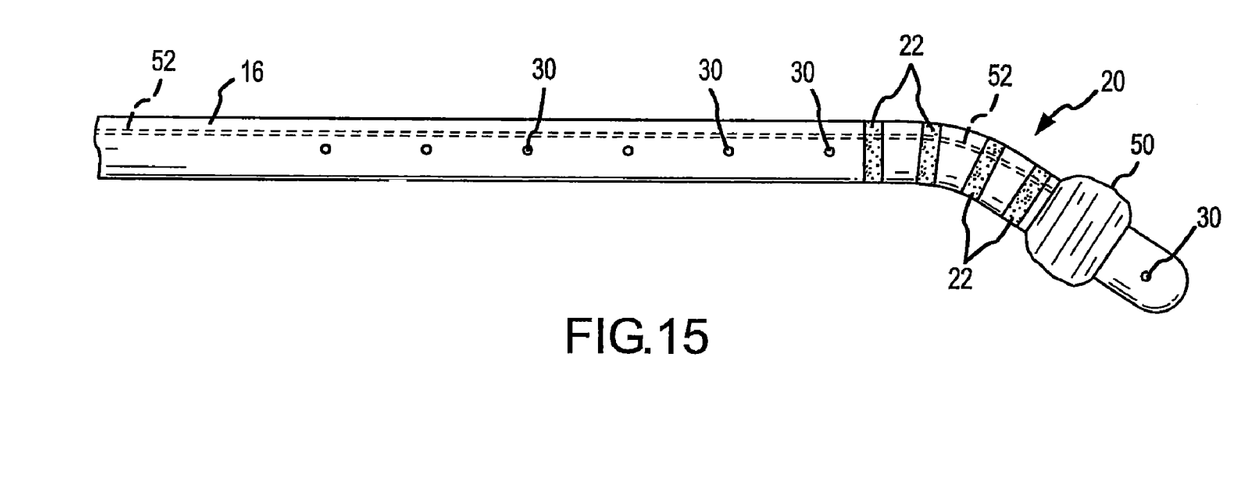
FIG. 15 illustrates yet a further embodiment of the present invention wherein an inflatable member is provided near the distal end of the stimulation lead to help anchor the lead after emplacement.

Referring to FIG. 15, yet another embodiment of the present invention is provided which further includes an inflatable portion 50 in the form of a bladder or balloon that is selectively inflated or deflated by an inflation line 52 extending conterminously with the central lumen. The inflatable portion is mounted to the exterior surface of the stimulation lead, and the inflation line 52 extends through an opening (not shown) in the sidewall of the lead that is covered by the inflatable portion 50. The inflation line 52 communicates with a source of compressed fluid (not shown), and the physician may inflate the inflatable portion 50 to a desired size. As also shown, the inflatable portion 50 is preferably placed along a location of the stimulation lead that does not cover or block any infusion ports 30, as well as any electrodes 22.

Figure 16:
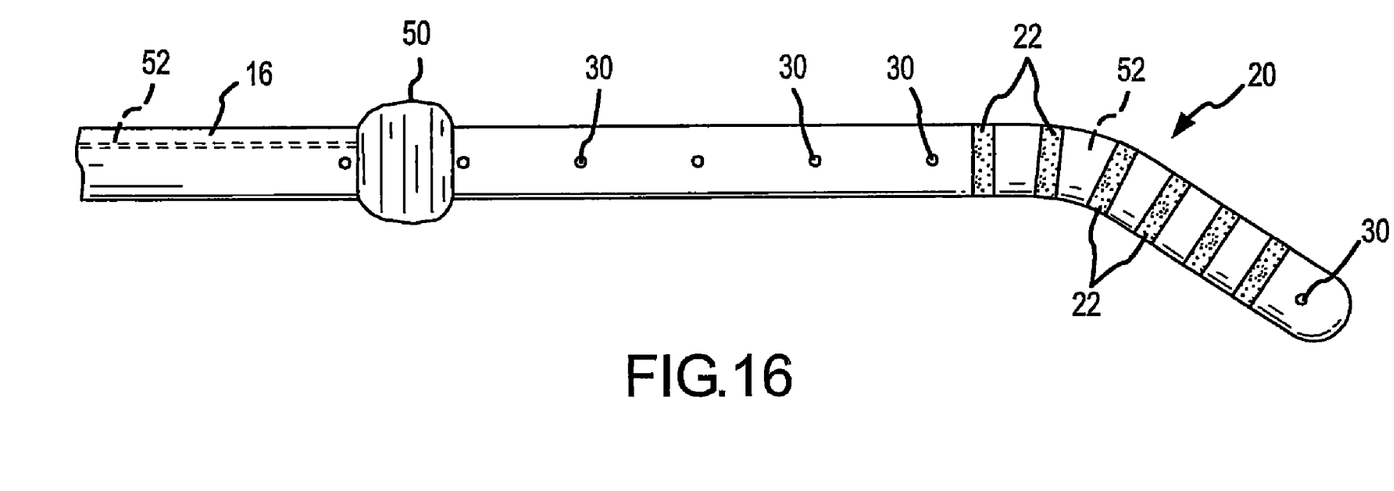
FIG. 16 illustrates the embodiment of FIG. 15 but the inflatable member being provided near the proximal end of the stimulation lead.

In some instances, the stimulation lead may reside within a patient for an extended period of time. As time passes, the stimulation lead may have a tendency to migrate or drift within the disc. Drifting of the stimulation lead can be problematic for a number of reasons, to include causing damage to the disc by penetration of the distal tip of the stimulation lead completely through the disc, as well as drifting of the stimulation lead so that it is no longer centered around/along the desired area of the disc to be treated. To maintain the stimulation lead in its desired position after the stimulation has been emplaced, the inflatable portion 50 may be inflated to the desired size, thereby serving as an anchor to help prevent drifting of the stimulation lead within the disc. In most instances, it is desirable to place the inflatable portion 50 near the distal tip of the stimulation lead to best prevent undesired drift of the stimulation lead; however, it is also contemplated within the present invention that the inflatable portion 50 may be selectively placed along other areas of the stimulation lead to best serve as an anchor. For example, as shown in FIG. 16, the inflatable portion is located at the proximal end of the stimulation lead. Furthermore, it may be desirable to incorporate both a distally located inflation portion 50, and another inflation portion located at the proximal end of the device that would further help to prevent the stimulation lead from drifting or from being inadvertently removed.

Some disc tissue may have a tendency to adhere to a stimulation lead that has been emplaced within the disc for a long period of time, and/or the disc tissue may have a tendency to harden around the emplaced stimulation lead thereby making it more difficult to remove the stimulation lead. Thus, it is also contemplated within the present invention that the inflatable portion 50 could be provided to extend along a much greater distance of the stimulation lead, and the inflatable portion 50 could be inflated to a desired level prior to the stimulation lead being emplaced within a disc. When it is then desired to remove the stimulation lead, the inflatable portion could be deflated which would create a small gap or space between the surrounding disc tissue and the stimulation lead thereby easing removal of the stimulation lead.

Thus, the inflatable portion 50 can be used either as an anchor to maintain positioning of the stimulation lead within the disc, or the inflatable portion 50 can be used in a reverse role by enlarging the overall size of the stimulation lead once emplaced, but then reducing the overall size of the stimulation lead by deflating the inflatable portion when it is desired to remove the stimulation lead.

Figure 17:
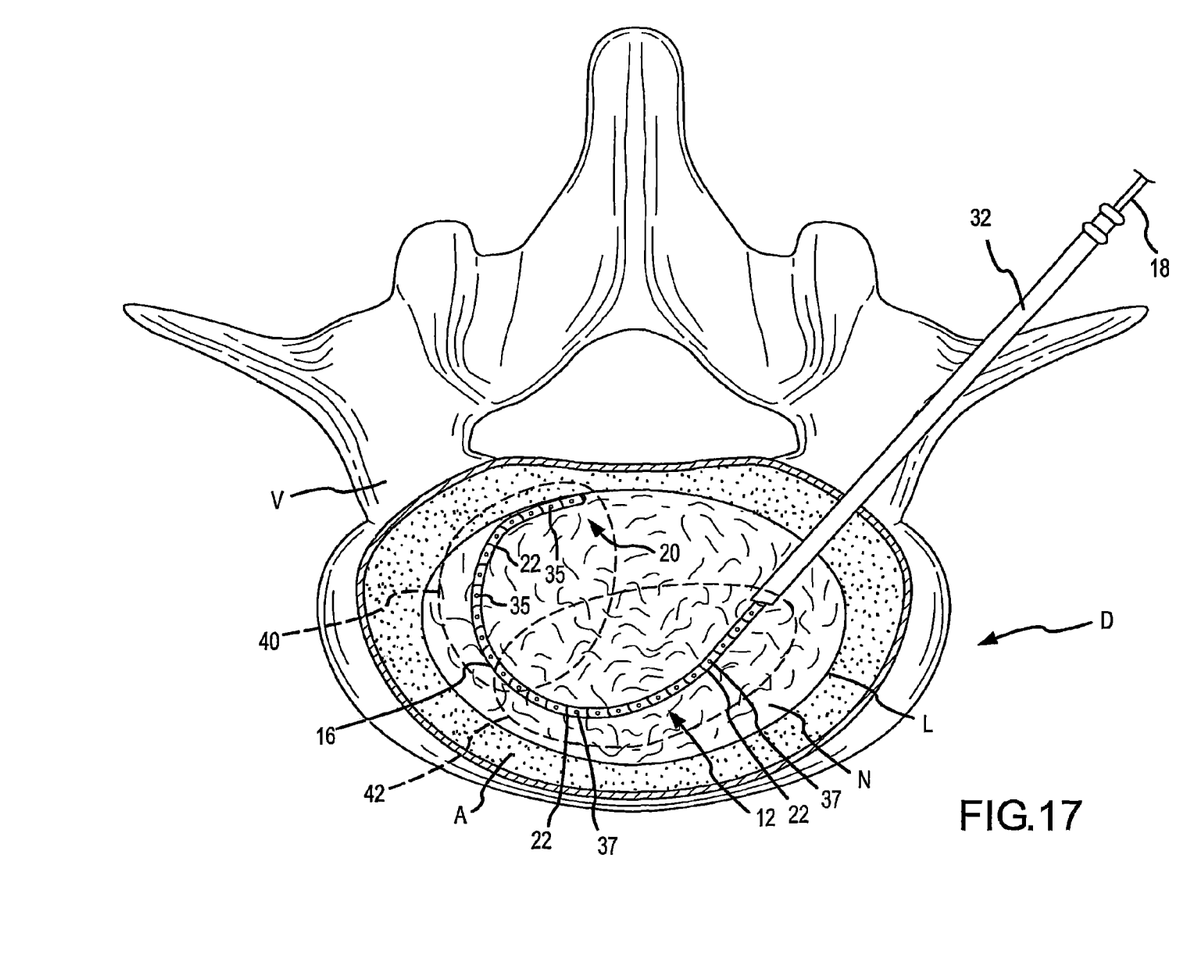
FIG. 17 illustrates the stimulation lead of FIG. 14 inserted in an invertebral disc wherein the lead can selectively treat two targeted treatment zones or areas within the disc.

Referring to FIG. 17, a stimulation lead is shown emplaced within a disc D, the stimulation lead generally corresponding to the embodiment shown in FIG. 14. Two oval shaped areas 40 and 42 are shown surrounding the distal and proximal sections of the stimulation lead, respectively. These areas 40 and 42 may generally represent targeted treatment areas within the disc. In accordance with the embodiment of FIG. 14, the physician has the option of applying different infusion materials through the separate sets of infusion ports 35 and 37 to specifically target the tissue located within the areas 40 and 42. Such treatment could be simultaneous, sequential, or any combination thereof. Furthermore, as mentioned above, selected sets of electrodes could be energized to provide treatment. For example, the electrodes may be wired so that the physician has the ability to energize two primary sets of electrodes, one set providing an electromagnetic field generated to cover area 40, and the other set providing an electromagnetic field to cover area 42. The electrodes may be wired and configured to provide generation of electromagnetic fields in any desired pattern along the length of the lead.

Figure 18:
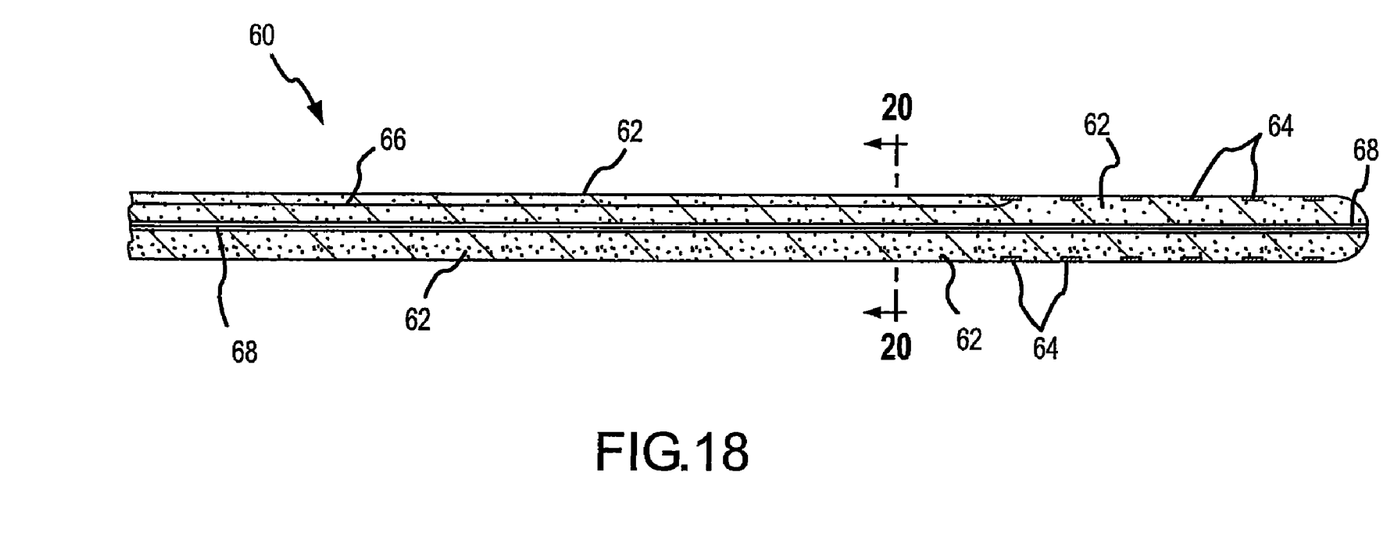
FIG. 18 illustrates a cross section of yet a further embodiment of the present invention wherein the body of the stimulation lead is made from a dissolvable matrix with the stimulating electrical contacts embedded therein.
Figure 19:
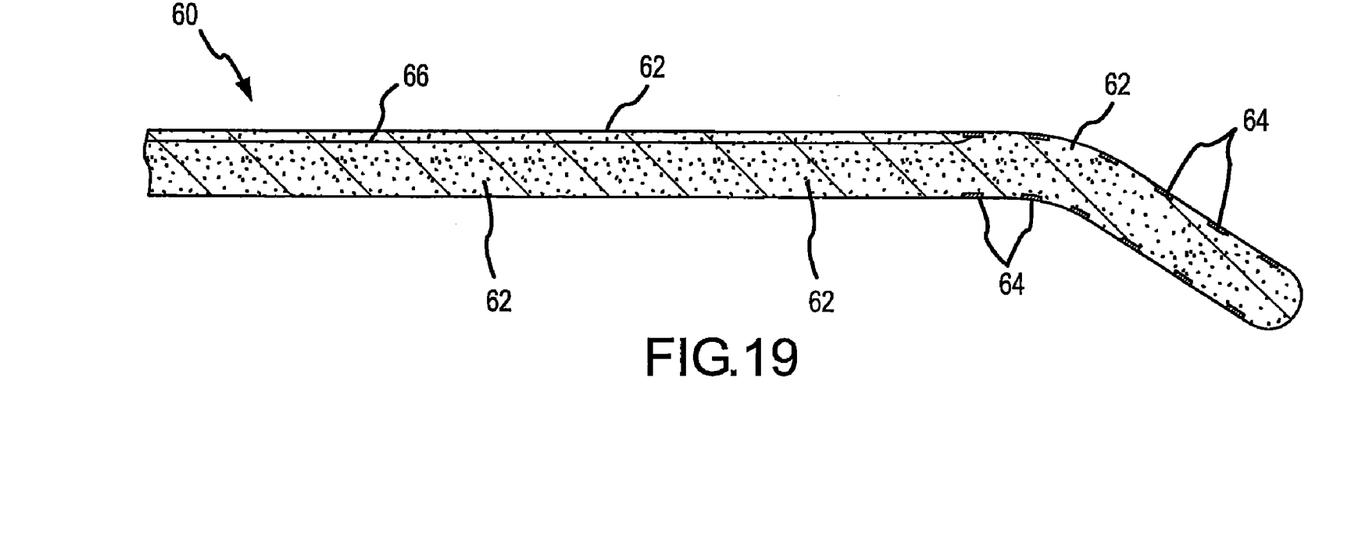
FIG. 19 illustrates a cross section of a further variation of the embodiment of FIG. 18 wherein the stimulation lead has a preconfigured bend at the distal end thereof and no central lumen.
Figure 20:
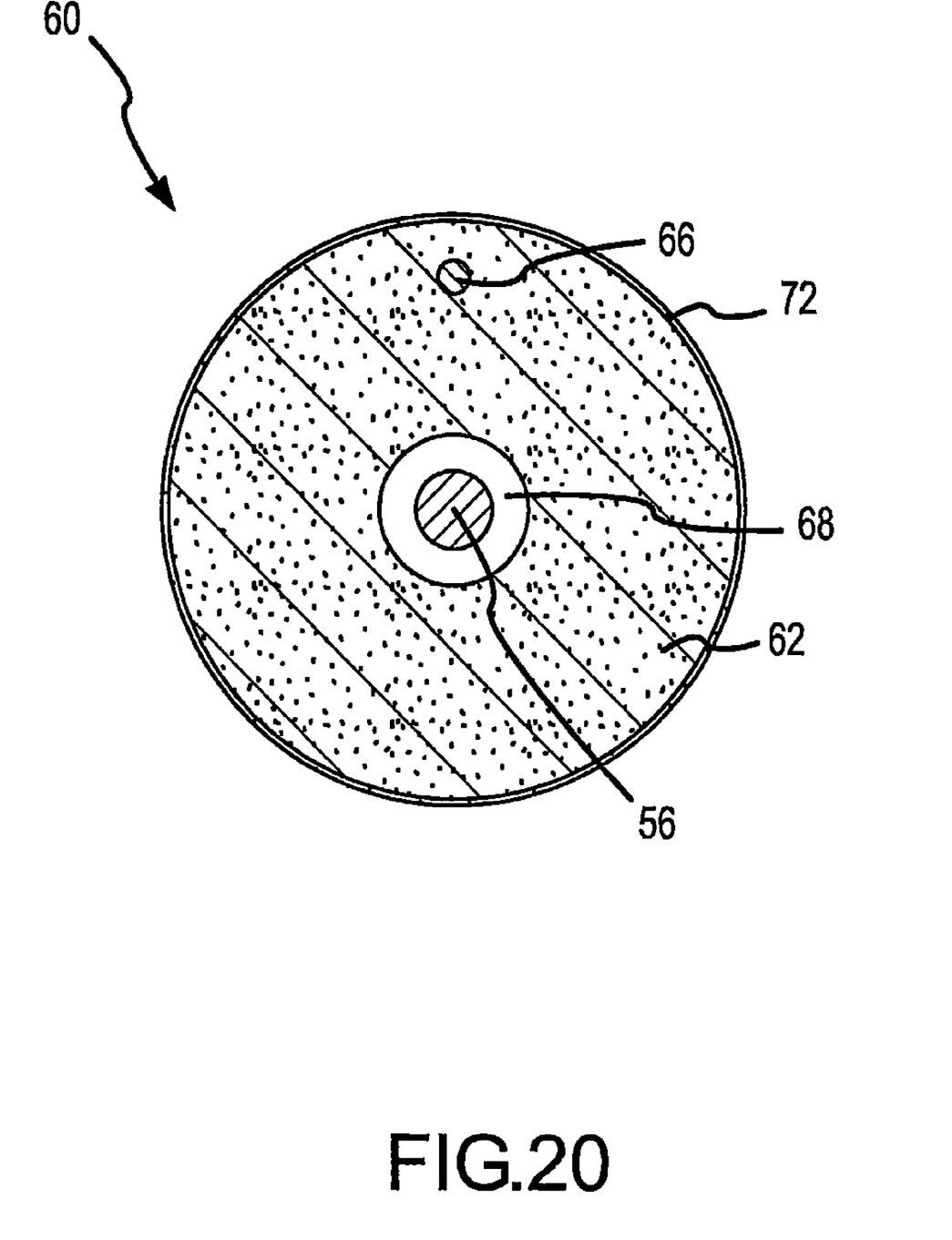
FIG. 20 is a cross-section taken along line 20-20 of FIG. 18, and further illustrating the use of an outer membrane which may help maintain the integrity of the stimulation lead when emplaced, as well as to control the rate at which the constituents incorporated within the dissolvable matrix are allowed to diffuse into the invertebral disc.

Referring now to FIGS. 18-20, yet another embodiment of the present invention is illustrated in the form of stimulation lead 60. For some treatments, it may be necessary to leave the stimulation lead emplaced within the invertebral disc for an extended period of time; however, for various reasons, it may not be possible to keep the stimulation lead emplaced for the amount of time to provide optimal treatment. In order to solve this particular problem, the embodiment of FIG. 18 contemplates the use of various chemical agents/medications and nutrients incorporated within a dissolvable matrix that forms the body 62 of the stimulation lead 60. The electrodes 64 as well as the conductor(s) 66 could be formed with the dissolvable matrix in a molding process whereby a particular shape and size stimulation lead could be produced. The electrodes 64 could function the same as the electrodes 22 discussed above and could be produced in any desired pattern and wiring arrangement. The dissolvable matrix can be made of a material that is biomedically acceptable for enabling a time release of the chemical agents/medications and nutrients mixed within the matrix. The matrix is preferably a solid yet flexible material, allowing the stimulation lead to be steered with the use of an insertable stylet 56 which could be provided through the central lumen 68. However, it shall be understood that this central lumen 68 is optional, and the matrix may be manufactured of a material which is durable yet flexible enough allowing the practitioner to steer the stimulation lead without the use of a stylet. Accordingly, FIG. 19 illustrates another embodiment wherein there is no lumen present, and a predetermined bend angle is formed in the stimulation lead enabling the lead to take the desired path through the disc when emplaced. Once inserted into the disc, the matrix would dissolve and the regenerating chemicals/medications and nutrients would slowly diffuse into the surrounding disc tissue leaving only the electrodes 64 and conducting wire(s) 66 to be removed at some later time.

With the embodiment shown in FIGS. 18 and 19, an infusion pump would not be required, and would thereby also allow for the subcutaneously placed pulse generator (IPG) to be significantly smaller. Similar to the combined pump/pulse generator device described above, this much smaller pulse generator could be rechargeable, or be powered by a battery source as desired.

In a modification to the embodiment of FIG. 18, it is also contemplated within the scope of the present invention that a stimulation lead can simply comprise a dissolvable matrix having a desired combination of chemical agents/medications and nutrients, and no electrodes incorporated within the lead. In some cases, stimulation by an electromagnetic field may be unnecessary to achieve the desired regenerative and/or pain relieving disc response.

FIG. 20 illustrates the designated cross-section of the device in FIG. 18. Additionally, FIG. 20 illustrates the use of an optional outer membrane 72 which could serve multiple purposes. One purpose for the membrane 72 would be to support the structural integrity of the matrix material of the body 62, thereby providing additional support for when the stimulation lead was emplaced. Additionally, this membrane 72 could serve as an osmotic membrane to help meter the rate at which the chemical agents/medications and nutrients were allowed to diffuse into the surrounding tissue. Thus, in addition to the matrix having a predetermined rate of diffusion; the membrane 72 could be used as an additional means to control the rate at which the chemical agents/medications and nutrients were delivered to the surrounding tissue. It is further contemplated that if the membrane 72 is provided only for structural support to the lead when emplaced, the membrane could be made of a material that quickly dissolves after being emplaced within the disc and the diffusion rate would be entirely controlled by the particular diffusion characteristics of the matrix.

Based upon the foregoing, the present invention provides a combination electrical and stimulation lead especially adapted for treatment of disc ailments. The various embodiments provide a treating physician with stimulation leads of various configurations, which optimizes a physician's ability to precisely position the stimulation lead, as well as to precisely direct both electrical and chemical stimulation.

While the above description and drawings disclose and illustrate embodiments of the present invention, it should be understood that the invention is not limited to these embodiments. Those skilled in the art may make other modifications and changes employing the principles of the present invention, particularly considering the foregoing teachings. Therefore, by the appended claims, the applicant intends to cover such modifications and other embodiments.

What is claimed is:

1. A stimulation device especially adapted for inserting within an intervertebral disc for treatment of target tissue therein, said device comprising:
   a stimulation lead having an elongate, substantially tubular configuration defining a body of the stimulation lead, wherein the body of said stimulation lead has a proximal end configured to be connected to a pulse generator and a distal end configured to carry electrodes, the body including an exposed outer surface thereof is made of a matrix material including nutrients and medications intermixed therewith, said matrix being dissolvable within the intervertebral disc to deliver the medications and nutrients to a patient.

2. A stimulation device, as claimed in claim 1, wherein:
   said stimulation lead further includes a central lumen extending therethrough, and a stylet inserted within said lumen for assisting in steering of the stimulation lead when emplaced.

3. A stimulation device, as claimed in claim 1, wherein:
   said stimulation lead further includes a plurality of electrodes positioned on said stimulation lead, said electrodes communicating with a source of energy for providing electrical stimulation of tissue adjacent said electrodes.

4. A stimulation device, as claimed in claim 1, wherein:
   said stimulation lead further includes an outer membrane formed thereover.

5. A stimulation device, as claimed in claim 4, wherein:
   said membrane includes an osmotic membrane for controlling the rate at which said medication and nutrients are infused into the disc.

6. A device, as claimed in claim 1, wherein:
   said matrix is formed in a desired shape to assist in steering of said stimulation lead when emplaced within the disc.

7. A device, as claimed in claim 1, wherein:
   said medications and said nutrients are selected from the group consisting of glucose, glucosamine, chondroitin, oxygen, oxygenating agents, anti-oxidants, anti-glycosylating agents, pH buffers, anti-inflammatory agents, growth and differentiating factor-5 (GDF-5), transforming growth factor-beta (TGF-β), insulin-like growth factor-1 (IGF-1), and basic fibroblasts growth factor (bFGF).

8. A stimulation device especially adapted for placement within an intervertebral disc for treatment of target tissue therein, said device comprising:
a stimulation lead having a body with a proximal end configured to be connected to a pulse generator and a distal end configured to carry electrodes, the body including an exposed outer surface thereof made of a dissolvable matrix material that dissolves over a period of time when the stimulation lead is implanted within an intervertebral disc, and wherein the dissolvable matrix is composed of materials selected from the group consisting of nutrients and medications.

9. A stimulation device, as claimed in claim 8, wherein:
said stimulation lead further includes a plurality of electrodes positioned on said stimulation lead, said electrodes communicating with a source of energy for providing electrical stimulation of tissue adjacent said electrodes.

10. A stimulation device, as claimed in claim 8, wherein:
said stimulation lead further includes an outer membrane formed thereover.

11. A stimulation device, as claimed in claim 10, wherein:
said membrane includes an osmotic membrane for controlling a rate at which said materials are infused in the disc.

* * * * *